United States Patent
Liu et al.

(10) Patent No.: US 12,112,406 B2
(45) Date of Patent: Oct. 8, 2024

(54) ATTENTION MECHANISM-BASED LOW-DOSE DUAL-TRACER PET RECONSTRUCTION METHOD

(71) Applicant: Zhejiang University, Hangzhou (CN)

(72) Inventors: Huafeng Liu, Hangzhou (CN); Fuzhen Zeng, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 401 days.

(21) Appl. No.: 17/719,320

(22) Filed: Apr. 12, 2022

(65) Prior Publication Data

US 2022/0335665 A1 Oct. 20, 2022

Related U.S. Application Data

(63) Continuation-in-part of application No. PCT/CN2022/070203, filed on Jan. 5, 2022.

(30) Foreign Application Priority Data

Apr. 14, 2021 (CN) .......................... 202110397594.4

(51) Int. Cl.
*G06T 11/00* (2006.01)
*A61B 6/03* (2006.01)
*G16H 10/40* (2018.01)

(52) U.S. Cl.
CPC ............ *G06T 11/005* (2013.01); *A61B 6/037* (2013.01); *G06T 11/006* (2013.01); *G16H 10/40* (2018.01); *G06T 2211/421* (2013.01)

(58) Field of Classification Search
CPC ................. G06T 11/005; G06T 11/006; G06T 2211/421; G16H 10/40; A61B 6/037
See application file for complete search history.

(56) References Cited

U.S. PATENT DOCUMENTS

| | | | | |
|---|---|---|---|---|
| 2022/0130079 A1* | 4/2022 | Hu | ........................ | G06T 11/005 |
| 2022/0351431 A1* | 11/2022 | Liu | ........................ | G06N 3/094 |

FOREIGN PATENT DOCUMENTS

| | | | | |
|---|---|---|---|---|
| CN | 107133997 B | * | 10/2019 | ............... G06N 3/08 |
| CN | 111166368 A | * | 5/2020 | ............. A61B 6/037 |
| CN | 111920436 A | * | 11/2020 | |

* cited by examiner

*Primary Examiner* — Vu Le
*Assistant Examiner* — Jack Peter Kraynak
(74) *Attorney, Agent, or Firm* — MATTHIAS SCHOLL P.C.; Matthias Scholl

(57) ABSTRACT

An attention mechanism-based low-dose dual-tracer PET reconstruction method. The method achieves low-dose dual-tracer PET image reconstruction by an attention mechanism-based convolution network model, and estimates the standard dose and separates dual-tracer PET signals in a sinogram. With the help of deep learning, a feature extraction tool, the method can reconstruct standard-dose single-tracer PET images in a PET Low-Dose Dual-Tracer Sinogram.

10 Claims, 6 Drawing Sheets

ATTENTION MECHANISM-BASED LOW-DOSE DUAL-TRACER PET RECONSTRUCTION METHOD

CROSS-REFERENCE TO RELAYED APPLICATIONS

This application is a continuation-in-part of International Patent Application No. PCT/CN2022/070203 with an international filing date of Jan. 5, 2022, designating the United States, and further claims foreign priority benefits to Chinese Patent Application No. 202110397594.4 filed Apr. 14, 2021. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure belongs to the field of PET imaging, and more particularly to an attention mechanism-based low-dose dual-tracer PET reconstruction method.

Positron Emission Tomography (PET) is a diagnostic functional imaging technique that can detect physiochemical activities in human body. With this technique, physiological indexes related to diseases such as glucose metabolism, vascular disease and hypoxia in target tissues in human body can be obtained. The principle of PET is that a positron isotope labeled compound (tracer) is injected or taken orally into human body, and accumulated at parts with high demand for such compound according to the needs of physiological or pathological activities inside the human body; radionuclides decay to emit positrons that will annihilate when encountering free negative electrons inside the body, to produce two pairs of y photons with the same energy of 511 keV and approximately 180 degrees apart in the direction of motion; when the y photons are detected by a detector outside the body, the spatial-temporal distribution of the tracer in vivo can be obtained by correcting and reconstructing the obtained data, thus making pathological diagnosis based on such spatial-temporal distribution. Different tracers can monitor different physiological activities and thus diagnose different diseases. For example, ($^{18}$F)-fluorodeoxyglucose (FDG) is commonly used to detect whether glucose metabolism is high or, and ($^{62}$Cu)-ATSM may be used to detect the intensity of hypoxia.

All-round and multi-dimensional detection of vital activities is helpful to improve the accuracy of staging diagnosis and disease diagnosis, and also provides more valuable information for choosing a more reasonable and effective therapeutic schedule. Therefore, it is very meaningful and promising to realize dual-tracer or even multi-tracer PET. However, with the introduction of PET/CT instruments into clinical use, the problem of radiation is of concern to researchers. In order to obtain better reconstructed images with each tracer in multi-tracer PET, the total dose of tracers injected will be higher than that of a tracer in single-tracer PET. Thus, the study of low-dose multi-tracer PET image reconstruction algorithm may make the clinical application of multi-tracer PET possible.

At present, no results have been published on low-dose dual-tracer PET reconstruction, but low-dose imaging has been studied to some extent in the field of single-tracer PET. Low-dose PET images are characterized by high noise and low contrast, so the commonly used method is to reconstruct a PET low-dose activity map by a traditional iterative reconstruction method and then to post-process or filter the map. However, the obtained images are too smooth, resulting in the deterioration of spatial resolution and quantitative accuracy. Many deep learning-based methods have been proposed in recent years, but researchers mostly use a neural network as a post-processing tool to map the PET low-dose activity map to a PET standard-dose activity map. These methods include multi-modal image methods and mono-modal image methods, where the multi-modal image methods mainly work together with MRI images, while some of the mono-modal image methods employ a Cycle GAN and low-dose and standard-dose PET activity maps simultaneously, and some only employ low-dose PET images.

SUMMARY

The disclosure provides an attention mechanism-based low-dose dual-tracer PET reconstruction method, which realizes low-dose dual-tracer PET image reconstruction by an attention mechanism-based convolution network model, and estimates the standard dose and separates dual-tracer PET signals in a sinogram. With the help of deep learning, a feature extraction tool, the method can reconstruct standard-dose single-tracer PET images in a PET Low-Dose Dual-Tracer Sinogram.

An attention mechanism-based low-dose dual-tracer PET reconstruction method, comprises:

(1) performing dynamic PET scanning on biological tissues injected with a standard-dose tracer I to obtain a PET Standard-dose Single-tracer Sinogram (SSS1) corresponding to the tracer I; and performing dynamic PET scanning on biological tissues injected with a standard-dose tracer II to obtain a PET Standard-dose Single-tracer Sinogram (SSS2) corresponding to the tracer II at an interval of 5 half-lives of the tracer I, wherein the standard-dose generally refers to a dose that is able to reconstruct an activity map using a traditional reconstruction algorithm;

(2) calculating, by a PET reconstruction algorithm, PET Standard-dose Single-tracer Activity Maps 1 and 2 (SSA1 and SSA2) corresponding to the SSS1 and the SSS2, respectively;

(3) normalizing and superimposing the SSS1 and the SSS2 to form a PET Standard-dose Dual-tracer Sinogram (SDS); down-sampling the SSS1 and the SSS2 respectively to obtain PET Low-dose Single-tracer Sinograms 1 and 2 (LSS1 and LSS2), and superimposing the LSS1 and the LSS2 to form a PET Low-dose Dual-tracer Sinogram (LDS); and normalizing and superimposing the SSA1 and the SSA2 to form a PET Standard-dose Dual-tracer Activity Map (SDA);

(4) repeating (1) to (3) several times to obtain a plurality of samples, and dividing these samples into a train set, a validation set and a test set, where each set of samples comprises the SSS1, the SSS2, the SDS, the LDS, the SSA1, the SSA2 and the SDA;

(5) building an attention mechanism-based network model comprising a sinogram part and a reconstruction part, inputting the LDS in the samples of the train set into the sinogram part, and serving the SSS1 and the SSS2 in the corresponding set of samples as labels of the sinogram part, so as to pre-train the sinogram part;

(6) cascading the pre-trained sinogram part with the reconstruction part, inputting the LDS in the samples of the train set into the sinogram part, serving the SSS1 and the SSS2 in the corresponding set of samples as the labels of the sinogram part and the SSA1 and the SSA2 as labels of the reconstruction part, so as to train the entire network model; and (7) inputting the LDS in the samples of the test set into the trained network model to achieve low-dose dual-tracer PET image reconstruction and obtain corresponding reconstructed SSS1, SSS2, SSA1 and SSA2.

In a class of this embodiment, the half-lives of the two tracers I and II used in (1) are arbitrary, and the method is applicable even if the two tracers are labeled with identical radionuclides, and is robust to tracer combinations, individual differences and sampling protocols.

In a class of this embodiment, the sinogram part is used to convert the LDS to the SSS, to estimate the standard dose and separate dual-tracer signals simultaneously; and Filtered Back Projection-Net (FBP-Net) is adopted in the reconstruction part.

In a class of this embodiment, the network model operates as follows:

a) allowing the input LDS to pass through two convolution blocks in sequence to extract shallow features and enter a spatial attention module, where the spatial attention module makes statistics on a spatial distribution of an input feature map by two convolution layers to obtain an initial weight map of the same size as the feature map, normalizing the weight map by a Sigmoid layer, and multiplying the feature map input by the normalized weight map to obtain a new feature map;

b) extracting, by two convolution kernels, bin and angle information simultaneously of the feature map output by the spatial attention module, combining extracted feature information in a channel, and fusing the information by passing through two convolution layers in sequence and inputting the information to a channel attention module;

c) aggregating, by the channel attention module, spatial features of all channels of the input feature map by an average pooling layer and a max pooling layer respectively to obtain two spatial descriptors to represent the spatial feature distribution of different channels; combining the two spatial descriptors by a first fully connected layer and passing through an ReLU layer and a second fully connected layer in sequence to generate a weight for each channel; and normalizing the weight for each channel by the Sigmoid layer to generate a channel weight map; and d) multiplying the feature map input by the channel attention module by the normalized channel weight map to obtain a new feature map which is adjusted by one convolution layer, and respectively normalizing the two PET SSSs in the adjusted feature map as outputs of the sinogram part.

In a class of this embodiment, when the sinogram part is pre-trained in (5), the LDSs at different time frames is put in a channel of an input layer, so that the multi-frame information is fused together only in a single convolution, and temporal and spatial information of the sinogram is used simultaneously in a subsequent convolution; and the spatial attention module is concerned with the spatial information of the sinogram, while the channel attention module is concerned with the temporal information of the sinogram.

In a class of this embodiment, the sinogram part is pre-trained in (5) as follows: initializing network parameters of the sinogram part, the network parameters comprising a bias vector and weight matrix of each layer, a learning rate, an optimization algorithm and max iterations; inputting the LDSs in the train set into the sinogram part in batches and optimizing the network parameters using a loss function L, and continuously updating the network parameters of the sinogram part by Batch Gradient Descent until the loss function L converges or reaches the max iterations.

In a class of this embodiment, the entire network model is trained in (6) as follows: initializing network parameters of the entire network model, the network parameters comprising a bias vector and weight matrix of each layer, a learning rate, an optimization algorithm and max iterations; inputting the LDSs in the train set into the sinogram part of the network in batches and optimizing the network parameters using the loss function L, and continuously updating the network parameters of the entire network model by Batch Gradient Descent until the loss function L converges or reaches the max iterations.

In a class of this embodiment, the expression of the loss function L is as follows:

$$L = \operatorname*{argmin}_{\omega,b}\left[\alpha \cdot MSE(x, y) - \beta \cdot \ln\frac{1+SSIM(x, y)}{2} + \eta \cdot MSE(TV(x), TV(y))\right];$$

where x and y are the outputs and labels of the sinogram part or the entire network model, respectively, TV( ) is a total variation operator, MSE( ) is a mean square error operator, S SIM( ) is a structural similarity operator, $\alpha$, $\beta$ and $\eta$ are a weight factor of corresponding bound terms, respectively, $\omega$ and b are a weight matrix and the bias vector of the sinogram part or the entire network model, respectively.

In a class of this embodiment, after the entire network model is trained in (6), the network model is further validated and parameters thereof are fine-tuned by samples in the validation set.

The network model in the disclosure does not limit the dynamic PET sinograms and the frame number of the reconstructed PET image, so the low-dose dual-tracer PET reconstruction method in the disclosure can process PET image signals with different frames.

The following advantages are associated with the attention mechanism-based low-dose dual-tracer PET reconstruction method of the disclosure: (1) the network model in the disclosure is universally applicable, and the method in the disclosure is proven to be robust through experiments on individual differences, tracer combinations and sampling protocols; (2) the network model in the disclosure fuse the temporal and spatial information of the sinogram at the same time, which provides more and more reliable information for separating dual-tracer signals; (3) the network model in the disclosure can estimate the standard dose and separate the dual-tracer signals in the sinogram; and (4) the low-dose dual-tracer PET reconstruction in the disclosure is a new research field.

DETAILED DESCRIPTION

To further illustrate the disclosure, embodiments detailing an attention mechanism-based low-dose dual-tracer PET reconstruction method are described below. It should be noted that the following embodiments are intended to describe and not to limit the disclosure.

According to the disclosure, an attention mechanism-based low-dose dual-tracer pet reconstruction method is detailed as follow.

(1) Data preparation.

(1.1) Dynamic PET scanning is performed on biological tissues injected with a standard-dose tracer I to obtain a PET Standard-dose Single-tracer Sinogram (SSS1) corresponding to the tracer I; and dynamic PET scanning is performed on biological tissues injected with a standard-dose tracer II to obtain a PET Standard-dose Single-tracer Sinogram (SSS2) corresponding to the tracer II at an interval of 5 half-lives of the tracer I.

(1.2) PET Standard-dose Single-tracer Activity Maps 1 and 2 (SSA1 and SSA2) of the standard-dose single-tracers corresponding to the SSS1 and the SSS2, respectively are calculated using a PET reconstruction algorithm.

(1.3) The SSS1 and the SSS2 are normalized and superimposed to form a Standard-dose Dual-tracer Sinogram (SDS); the SSS1 and the SSS2 are down-sampled respectively to obtain Low-dose Single-tracer Sinograms 1 and 2 (LSS1 and LSS2), and the LSS1 and the LSS2 are superimposed to form a Low-dose Dual-tracer Sinogram (LDS); and the SSA1 and the SSA2 are normalized and superimposed to form a Standard-dose Dual-tracer Activity Map (SDA).

(1.4) Steps (1.1) to (1.3) are repeated several times to obtain a large number of PET Sinograms (SSS1/SSS2/SDS/LDS) and PET Activity Maps (SSA1/SSA2/SDA), and these data are divided into a train set, a validation set and a test set.

Figure 1:
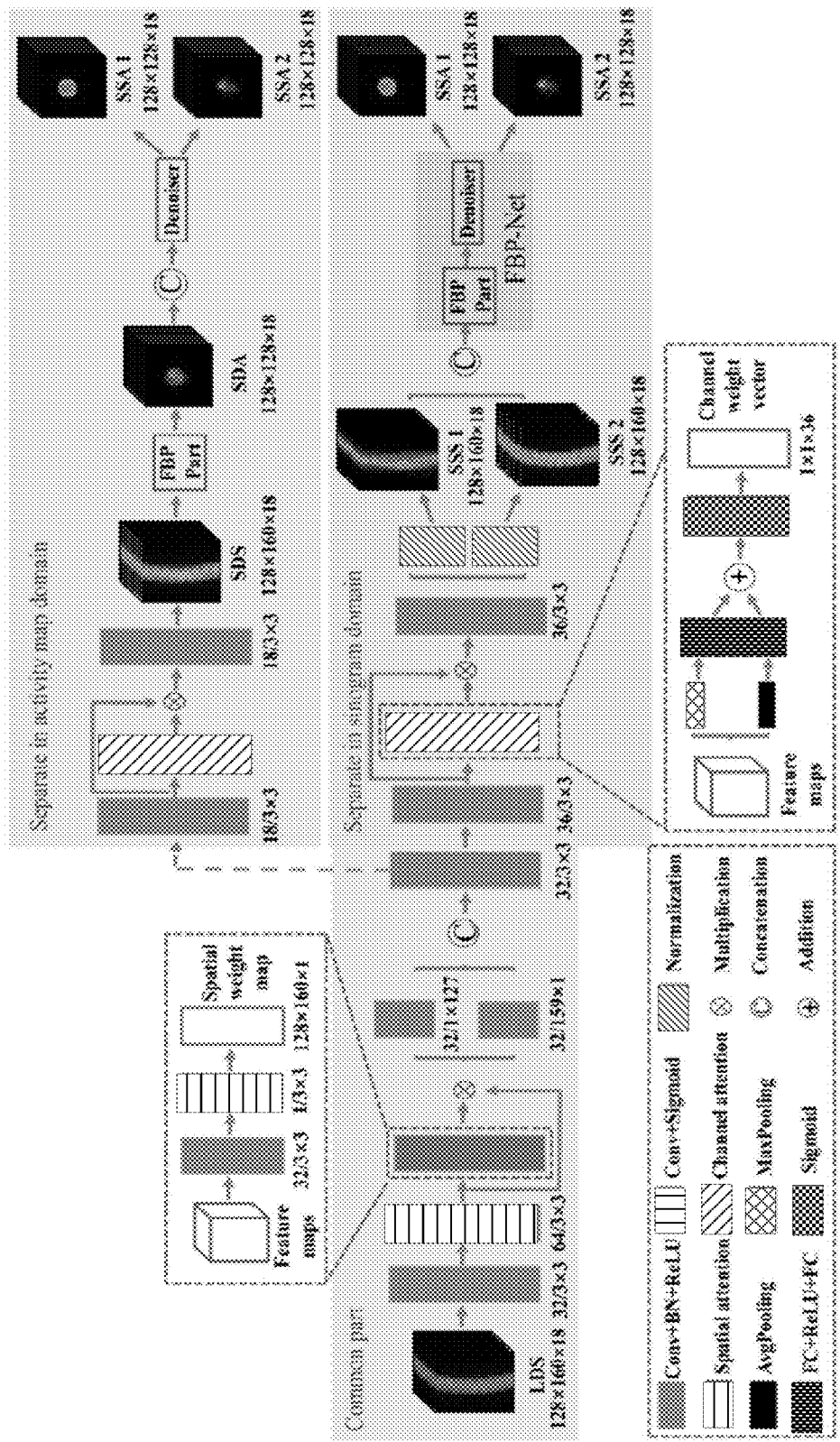
FIG. 1 is an attention mechanism-based network model according to the disclosure.

(2) A network is built for reconstruction of low-dose dual-tracer PET signals. As shown in FIG. 1, the network comprises encoding and decoding parts. A Conv+BN+ReLU block represents a module comprising a convolution layer, a BN layer and an ReLU layer, and the number of output channels and the size of a convolution kernel (the number of output channels/length×width of the convolution kernel) corresponding to the convolution layer are labeled below the module. The convolution layer also exists in the attention layer and is labeled in the same way. The size (length× width×the number of output channels) of a feature map output by each unlabeled color block is 128×160×number of output channels, except for 128×160×18, 128×160×1, 1×1× 36, and 128×128×18 as that of labeled ones, where the number of output channels in blocks with the convolution layer has been labeled and is the same as that in blocks without the convolution layer.

The input feature map enters a spatial attention module after being convolved twice to extract shallow features. According to the disclosure, the spatial attention module makes statistics on the spatial distribution of the feature map by two convolution layers to obtain an initial weight map of the same size as the feature map, normalizes the weight map by a Sigmoid layer, and finally multiplies the feature map input by the spatial weight map to obtain a new feature map.

According to the disclosure, in addition to the spatial attention module, two large convolution kernels are respectively used to extract bin and angle information simultaneously of the Sinogram, that is, to perform full connection in two directions to effectively extract information from the feature map adjusted by a spatial attention mechanism. Convolution is performed simultaneously in two directions, the obtained feature maps are stitched in a channel, and the information is fused by passing through the two convolution layers.

In the spatial attention mechanism, spatial features of all channels of the feature map are aggregated by an average pooling layer and a max pooling layer respectively to obtain two spatial descriptors of 1×1×(2×time frames) to represent the spatial feature distribution of different channels. The two spatial descriptors pass through a shared fully connected layer-ReLU layer-fully connected layer (FC-ReLU-FC) to generate a weight for each channel. Finally, the input of the channel attention module multiplies by a channel weight map to obtain a new feature map that is adjusted by passing through the convolution layer again. Finally, the obtained two SSSs are normalized respectively as the outputs of the sinogram part.

The Single-Tracer Sinogram estimated by the sinogram part can be reconstructed by any method. In this embodiment, FBP-Net is adopted for reconstruction. The SSSs are first estimated in the sinogram part, and stitched in a batch size dimension, i.e., images of the dual tracers are simultaneously reconstructed by FBP-Net.

(3) The train set is input into the network and trained by following steps.

(3.1) The network parameters, comprising the bias vector and weight matrix of each layer, the learning rate, the optimization method and the max iterations, are initialized.

(3.2) The LDSs in the train set are input into the sinogram part of the network in batches for training, and a loss function L between the outputs of the sinogram part and the labels SSS1 and SSS2 is calculated, and the parameters of the entire network are continuously updated by Batch Gradient Descent.

(3.3) The sinogram part and the reconstruction part are cascaded and trained together. The outputs of the sinogram part and the outputs of the reconstruction part are optimized by the loss function L until the loss function L converges or reaches the max iterations, so as to complete the training to obtain a low-dose dual-tracer PET reconstruction model.

The expression of the loss function L is as follows:

$$L = \underset{\omega, b}{\operatorname{argmin}} \left[ \alpha \cdot MSE(x, y) - \beta \cdot \ln \frac{1 + SSIM(x, y)}{2} + \eta \cdot MSE(TV(x), TV(y)) \right]$$

where ω and b represent Weight and Bias among model parameters, respectively, α, β and η represent proportionality factors of MSE, SSIM and TV constraints in the loss function, respectively, and x and y represent outputs and labels estimated by the model, respectively.

The disclosure is validated by simulation experiment as below.

(1) Template selection.

The train data are simulated by a 3D Zubal phantom with a size of 128×128×40.

Figure 2:
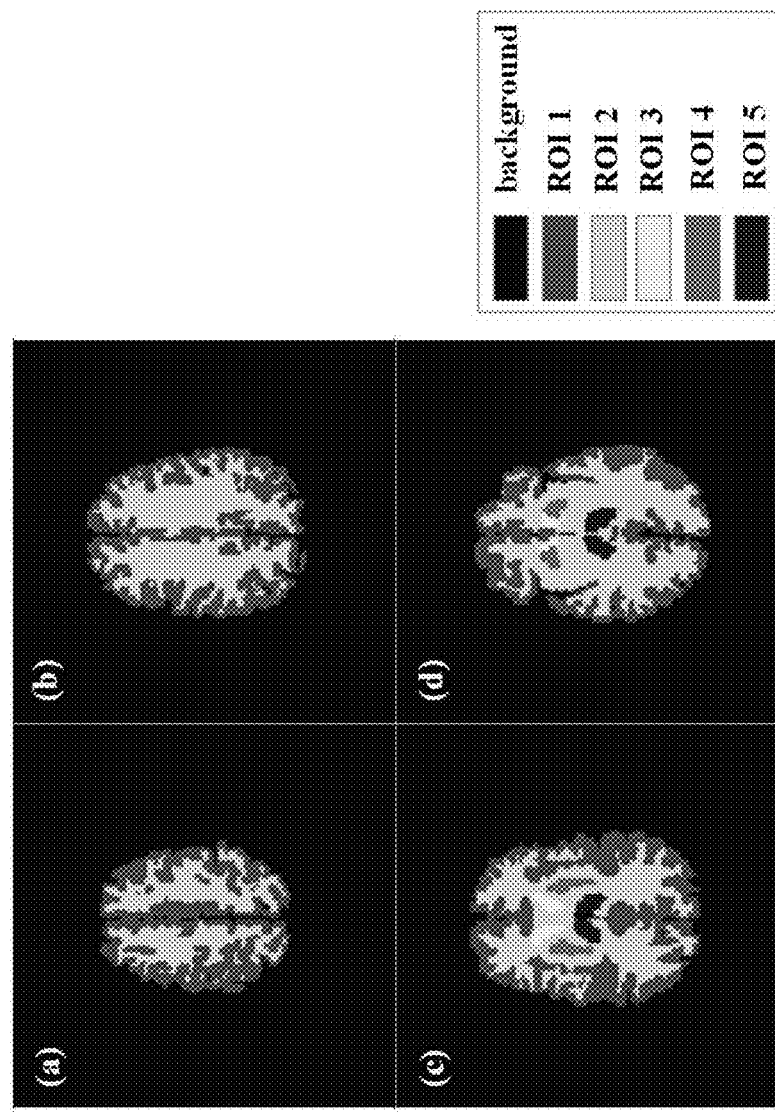
FIG. 2 shows slice maps of a Zubal phantom, in which (a) shows a $10^{th}$ slice, (b) shows a $20^{th}$ slice, (c) shows a $30^{th}$ slice and (d) shows a $40^{th}$ slice.

As shown in FIG. 2, (a), (b), (c) and (d) are shapes of $10^{th}$ $20^{th}$, $30^{th}$ and $40^{th}$ slices of the Zubal phantom selected in this experiment, respectively, and the whole phantom is divided into five Regions of Interest (ROI), with only two in the first 21 slices, three in the $22^{nd}$ to $27^{th}$ slices, and five in the remaining 13 slices.

(2) Simulation of the movement of the tracers in the human body.

The in-vivo movement of the two single tracers is simulated by a three-compartment model based on kinetic parameters, and a stable activity map of radionuclide after decay is solved by a dynamic differential equation.

(3) Simulation of PET scanning process.

The obtained activity map is projected by Fessler in Matlab and a simple system matrix only considering the geometric structure, and superimposed with 20% random noise at the same time, so as to obtain two single-tracer sinograms. During projection, the activity maps of all slices at all frame are projected one by one, and the size of the sinogram is 128×160×18, where 128 represents the number of bins, 160 represents the number of angles and 18 represents the number of time frames in one sinogram.

(4) Training process.

The LDSs in the train set are input into the network, and the corresponding SSS1, SSS2, SSA1 and SSA2 serve as labels in the sinogram part and the reconstruction part to provide feedback for tuning parameters of the entire network.

(5) Testing process.

The LDSs in the test set are input into the network, and the effectiveness of the network is described based on the results of the test set.

Figure 3:
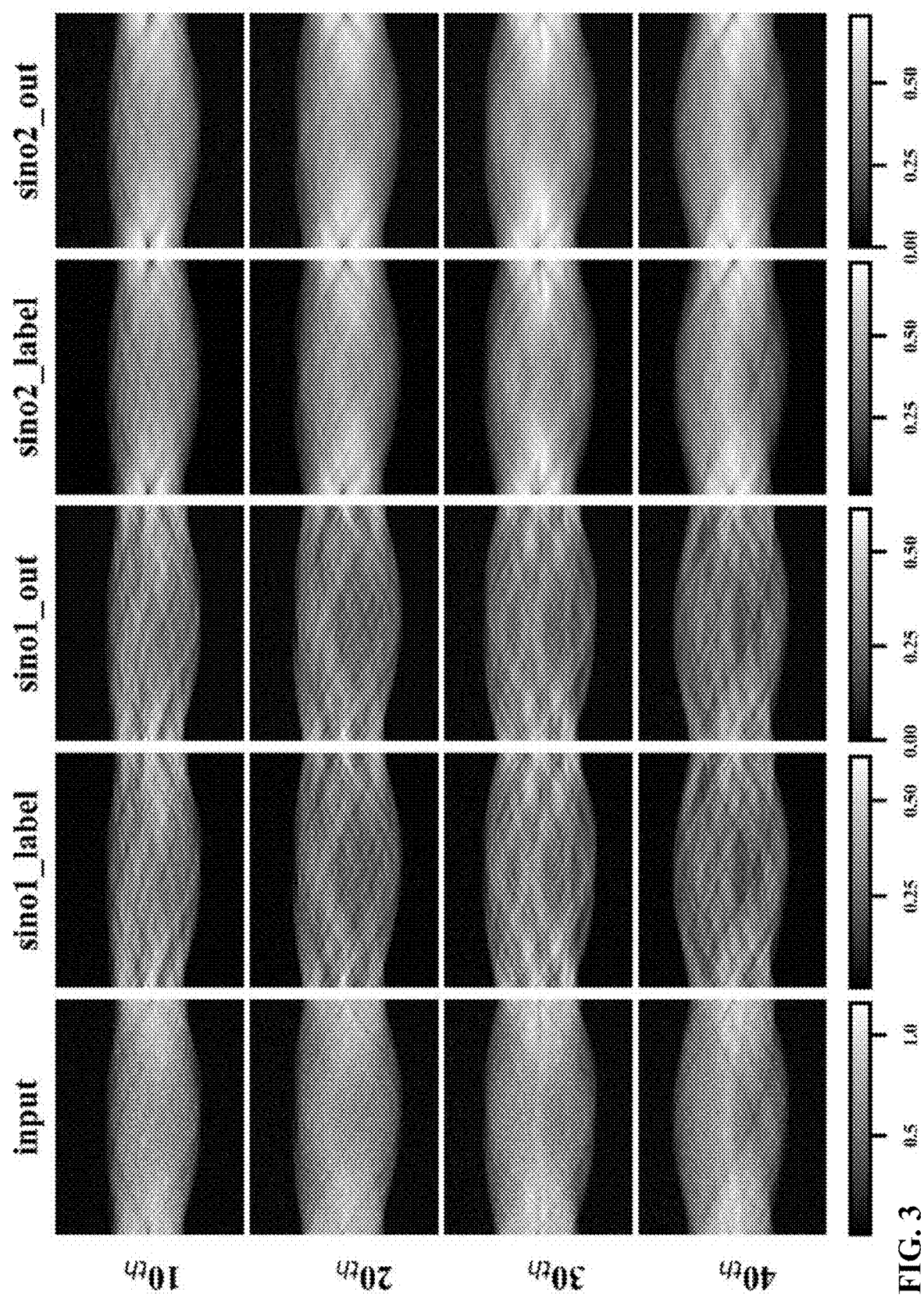
FIG. 3 is a standard-dose sinogram in case of 10% variation in kinetic parameters in an experiment on individual differences, showing $13^{th}$ frames of the $10^{th}$, $20^{th}$, $30^{th}$ and $40^{th}$ slices from the top down, as well as input LDSs (input), labels (label) of SSSs of tracers 1 and 2 and outputs (out) of the model from left to right, respectively.
Figure 4:
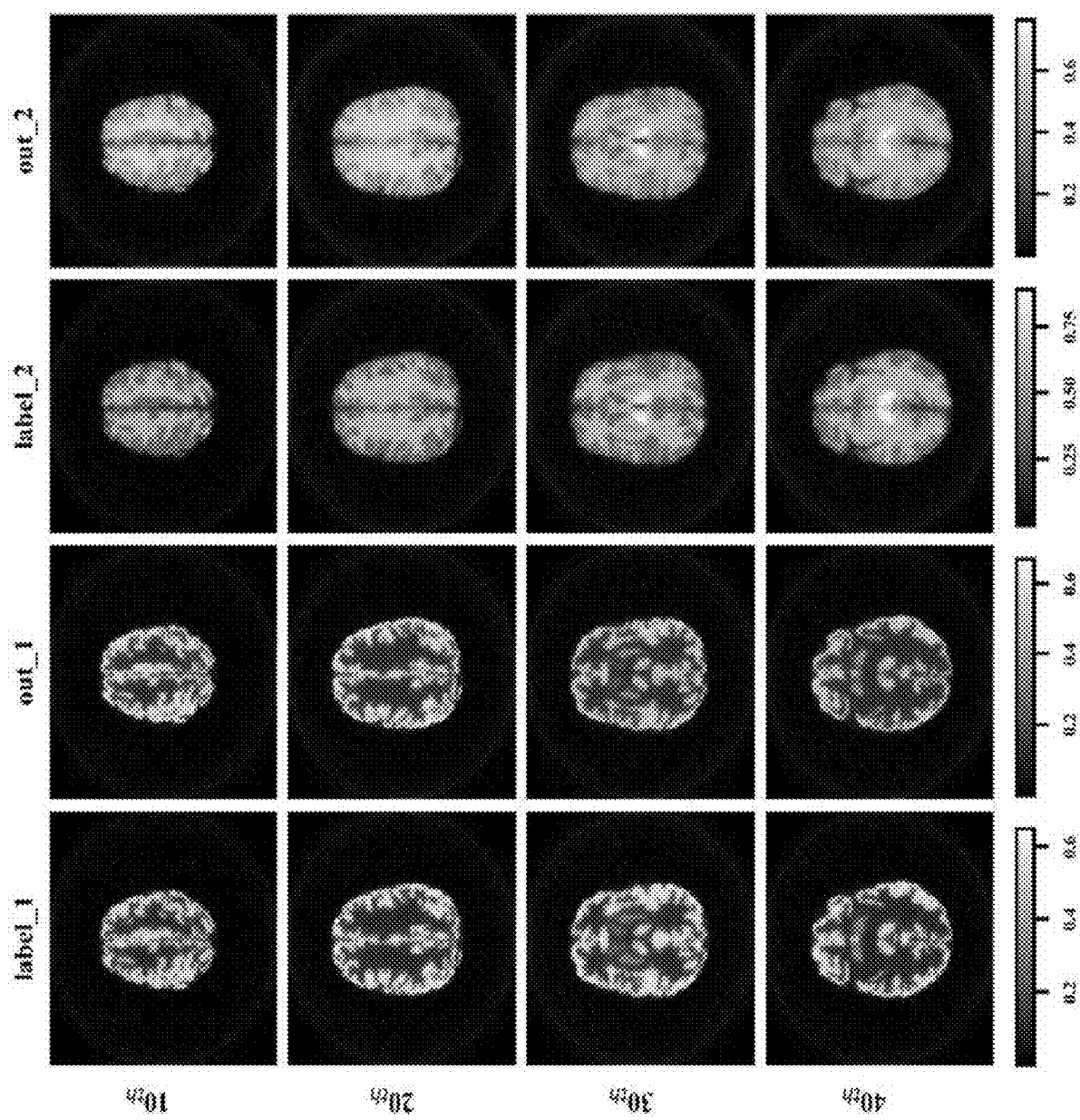
FIG. 4 is a PET activity map in case of 10% variation in the kinetic parameters in an experiment on individual differences, showing 13$^{th}$ frames of the 10$^{th}$ 20$^{th}$, 30$^{th}$ and 40$^{th}$ slices from the top down, as well as labels (label) of tracers 1 and 2 and outputs (out) of a method according to the disclosure, respectively.
Figure 5:
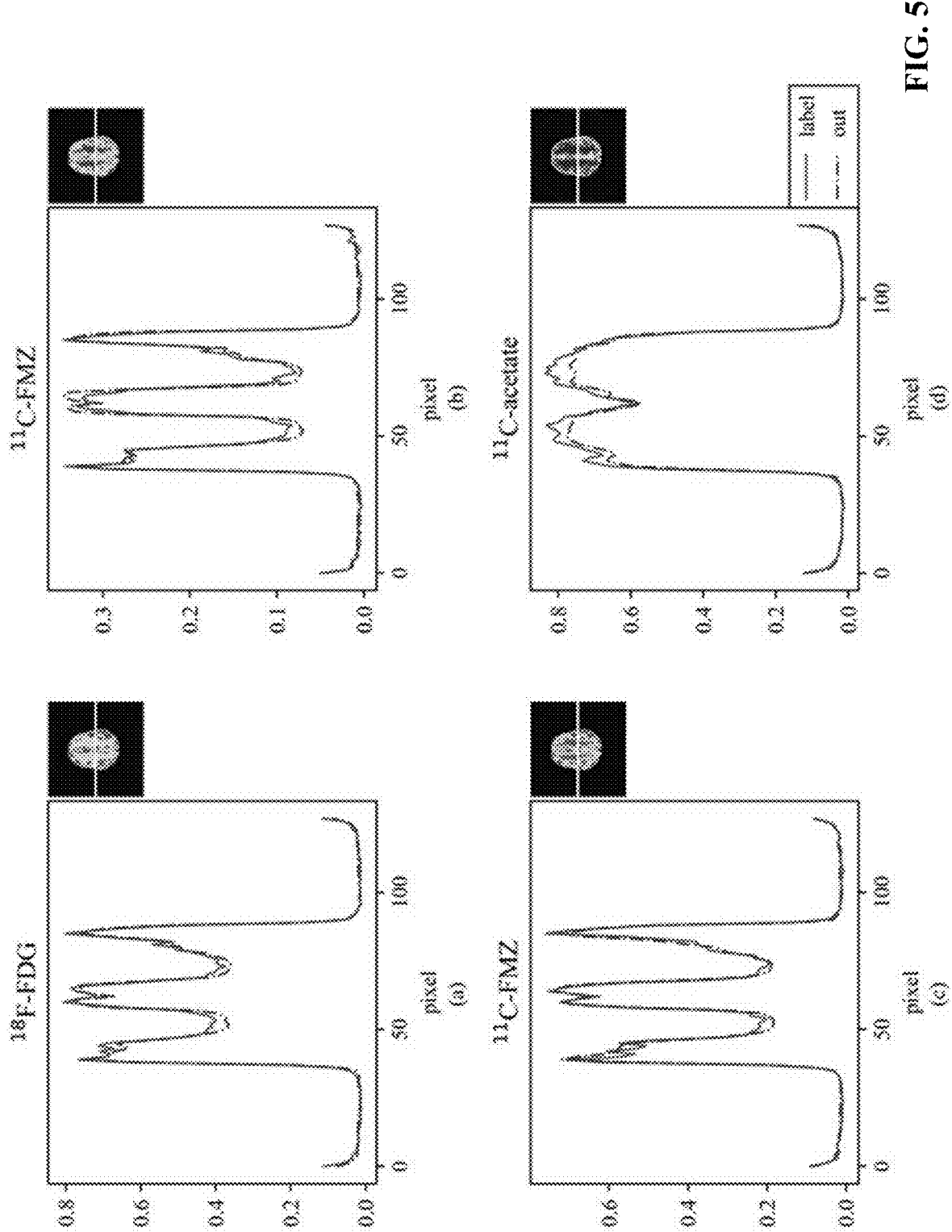
FIG. 5 shows PET activity profiles in an experiment on tracer combinations, in which (a) and (b) are PET activity profiles of the tracers I and II in a first tracer combination, and (c) and (d) are PET activity profiles of the tracer I and II in a second tracer combination.
Figure 6:
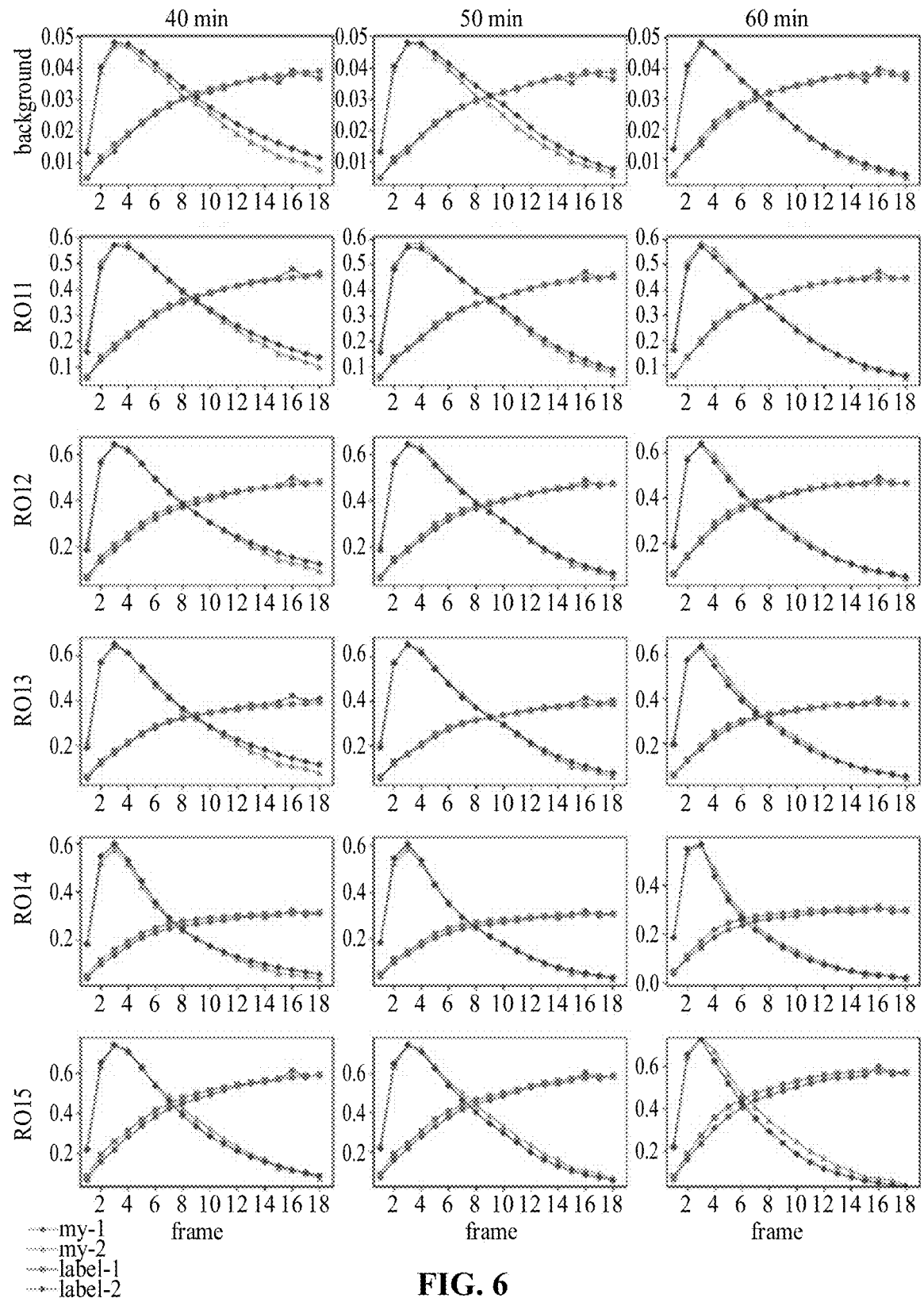
FIG. 6 shows TAC curve diagrams in an experiment on sampling protocols, showing a background and 5 Regions of Interest (ROI) respectively from the top down, and three sampling protocols of 40 min, 50 min and 60 min respectively from left to right; there are four curves in each child diagram, in which my-1 and my-2 respectively represent TAC of outputs of the tracers I and II estimated by the model according to the disclosure, and label-1 and label-2 respectively represent TAC of labels of the tracers I and II.

FIG. 3 is a comparison between outputs and labels of the sinogram part in an experiment on individual differences, FIG. 4 is a comparison between outputs and labels of the reconstruction part in an experiment on individual differences, FIG. 5 is a profile comparison between final outputs and labels of this method in an experiment on tracer combinations, and FIG. 6 is a TAC comparison between final outputs and labels of this method in an experiment on sampling protocols.

According to the figures, the comparison between outputs and labels estimated in the disclosure shows that the attention mechanism-based network built can well realize low-dose dual-tracer PET reconstruction, and is robust to individual differences, tracer combinations and sampling protocols, thus confirming the effectiveness and great potential of the method in the disclosure.

It will be obvious to those skilled in the art that changes and modifications may be made, and therefore, the aim in the appended claims is to cover all such changes and modifications.

What is claimed is:

1. A method, comprising:
   (1) performing dynamic PET scanning on biological tissues injected with a standard-dose tracer I to obtain a PET Standard-dose Single-tracer Sinogram (SSS1) corresponding to the tracer I; and performing dynamic PET scanning on biological tissues injected only with a standard-dose tracer II to obtain a PET Standard-dose Single-tracer Sinogram (SSS2) corresponding to the tracer II at an interval of 5 half-lives of the tracer I, wherein the standard-dose generally refers to a dose that is able to reconstruct an activity map using a traditional reconstruction algorithm;
   (2) calculating, by a PET reconstruction algorithm, PET Standard-dose Single-tracer Activity Maps 1 and 2 (SSA1 and SSA2) corresponding to the SSS1 and the SSS2, respectively;
   (3) normalizing and superimposing the SSS1 and the SSS2 to form a PET Standard-dose Dual-tracer Sinogram (SDS); down-sampling the SSS1 and the SSS2 respectively to obtain PET Low-dose Single-tracer Sinograms 1 and 2 (LSS1 and LSS2), and superimposing the LSS1 and the LSS2 to form a PET Low-dose Dual-tracer Sinogram (LDS); and normalizing and superimposing the SSA1 and the SSA2 to form a PET Standard-dose Dual-tracer Activity Map (SDA);
   (4) repeating (1) to (3) several times to obtain a plurality of samples, and dividing these samples into a train set, a validation set and a test set, where each set of samples comprises the SSS1, the SSS2, the SDS, the LDS, the SSA1, the SSA2 and the SDA;
   (5) building an attention mechanism-based network model comprising a sinogram part and a reconstruction part, inputting the LDS in the samples of the train set into the sinogram part, and serving the SSS1 and the SSS2 in the corresponding set of samples as labels of the sinogram part, so as to pre-train the sinogram part;
   (6) cascading the pre-trained sinogram part with the reconstruction part, inputting the LDS in the samples of the train set into the sinogram part, serving the SSS1 and the SSS2 in the corresponding set of samples as the labels of the sinogram part and the SSA1 and the SSA2 as labels of the reconstruction part, so as to train the entire network model; and
   (7) inputting the LDS in the samples of the test set into the trained network model to achieve low-dose dual-tracer PET image reconstruction and obtain corresponding reconstructed SSS1, SSS2, SSA1 and SSA2.

2. The method of claim 1, wherein the half-lives of the two tracers I and II used in (1) are arbitrary, and the method is applicable even if the two tracers are labeled with identical radionuclides, and is robust to tracer combinations, individual differences and sampling protocols.

3. The method of claim 1, wherein the sinogram part is used to convert the LDS to the SSS, to estimate a standard dose and separate dual-tracer signals simultaneously; and Filtered Back Projection-Net (FBP-Net) is adopted in the reconstruction part.

4. The method of claim 1, wherein the network model operates as follows:
   a) allowing the input LDS to pass through two convolution blocks in sequence to extract shallow features and enter a spatial attention module, where the spatial attention module makes statistics on a spatial distribution of an input feature map by two convolution layers to obtain an initial weight map of the same size as the feature map, normalizing the weight map by a Sigmoid layer, and multiplying the feature map input by the normalized weight map to obtain a new feature map;
   b) extracting, by two convolution kernels, bin and angle information simultaneously of the feature map output by the spatial attention module, combining extracted feature information in a channel, and fusing the information by passing through two convolution layers in sequence and inputting the information to a channel attention module;

c) aggregating, by the channel attention module, spatial features of all channels of the input feature map by an average pooling layer and a max pooling layer respectively to obtain two spatial descriptors to represent the spatial feature distribution of different channels; combining the two spatial descriptors by a first fully connected layer and passing through an ReLU layer and a second fully connected layer in sequence to generate a weight for each channel; and normalizing the weight for each channel by the Sigmoid layer to generate a channel weight map; and d) multiplying the feature map input by the channel attention module by the normalized channel weight map to obtain a new feature map which is adjusted by one convolution layer, and respectively normalizing the two PET SSSS in the adjusted feature map as outputs of the sinogram part.

5. The method of claim 1, wherein when the sinogram part is pre-trained in (5), the LDSs at different time frames is put in a channel of an input layer, so that multi-frame information is fused together only in a single convolution, and temporal and spatial information of the sinogram is used simultaneously in a subsequent convolution; and the spatial attention module is concerned with the spatial information of the sinogram, while the channel attention module is concerned with the temporal information of the sinogram.

6. The method of claim 1, wherein the sinogram part is pre-trained in (5) as follows: initializing network parameters of the sinogram part, the network parameters comprising a bias vector and weight matrix of each layer, a learning rate, an optimization algorithm and max iterations; inputting the LDSs in the train set into the sinogram part in batches and optimizing the network parameters using a loss function L, and continuously updating the network parameters of the sinogram part by Batch Gradient Descent until the loss function L converges or reaches the max iterations.

7. The method of claim 1, wherein the entire network model is trained in (6) as follows: initializing network parameters of the entire network model, the network parameters comprising a bias vector and weight matrix of each layer, a learning rate, an optimization algorithm and max iterations; inputting the LDSs in the train set into the sinogram part of the network in batches and optimizing the network parameters using the loss function L, and continuously updating the network parameters of the entire network model by Batch Gradient Descent until the loss function L converges or reaches the max iterations.

8. The method of claim 6, wherein the loss function L is expressed as follows:

$$L = \operatorname*{argmin}_{\omega,b}\left[\alpha \cdot MSE(x, y) - \beta \cdot \ln\frac{1 + SSIM(x, y)}{2} + \eta \cdot MSE(TV(x), TV(y))\right];$$

where x and y are outputs and labels of the sinogram part or the entire network model, respectively; TV( ) is a total variation operator, MSE( ) is a mean square error operator, SSIM( ) is a structural similarity operator, $\alpha$, $\beta$ and $\eta$ are a weight factor of corresponding bound terms, respectively; $\omega$ and b are a weight matrix and the bias vector of the sinogram part or the entire network model, respectively.

9. The method of claim 7, wherein the loss function L is expressed as follows:

$$L = \operatorname*{argmin}_{\omega,b}\left[\alpha \cdot MSE(x, y) - \beta \cdot \ln\frac{1 + SSIM(x, y)}{2} + \eta \cdot MSE(TV(x), TV(y))\right];$$

where x and y are outputs and labels of the sinogram part or the entire network model, respectively; TV( ) is a total variation operator, MSE( ) is a mean square error operator, SSIM( ) is a structural similarity operator, $\alpha$, $\beta$ and $\eta$ are a weight factor of corresponding bound terms, respectively; $\omega$ and b are a weight matrix and the bias vector of the sinogram part or the entire network model, respectively.

10. The method of claim 1, wherein after the entire network model is trained in (6), the network model is further validated and parameters thereof are fine-tuned by samples in the validation set.

* * * * *